United States Patent [19]

Küster et al.

[11] 4,312,998
[45] * Jan. 26, 1982

[54] METHOD FOR MAKING N-SUBSTITUTED ACRYLAMIDES

[75] Inventors: Erich Küster, Krefeld; Bernhard Goossens, Velbert; Kurt Dahmen, Monchengladbach; Eduard Barthell, Krefeld, all of Fed. Rep. of Germany

[73] Assignee: Chemische Fabrik, Cologne, Fed. Rep. of Germany

[*] Notice: The portion of the term of this patent subsequent to Dec. 2, 1997, has been disclaimed.

[21] Appl. No.: 145,660

[22] Filed: May 2, 1980

[30] Foreign Application Priority Data

May 8, 1979 [DE] Fed. Rep. of Germany ....... 2918486

[51] Int. Cl.³ .............................................. C07C 102/00
[52] U.S. Cl. ................................................... 564/205
[58] Field of Search .................... 260/561 N; 564/205

[56] References Cited

U.S. PATENT DOCUMENTS 3,878,247  4/1975  Moss et al. ..................... 260/561 N
3,914,303  10/1975  Daniher ........................ 260/561 N
4,237,067  12/1980  Küster et al. ....................... 564/205

OTHER PUBLICATIONS

Becker et al., Journal f. prokt. Chemie Band 316, Heft 6, 1974, pp. 1013-1029.

Primary Examiner—Arthur P. Demers
Attorney, Agent, or Firm—Sprung, Felfe, Horn, Lynch & Kramer

[57] ABSTRACT

The invention relates to a process for the preparation of N-substituted acrylamides of the general formula

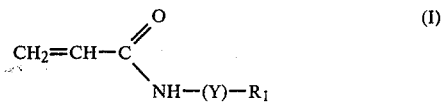

wherein Y denotes a bivalent straight - or branched chain radical with 2 to 30, preferably 2 to 18, and particularly 2 to 6 carbon atom-, preferably a group of the formula $(Y_1)_m\text{-}(Y_2)_n\text{-}(Y_3)_t$, in which $Y_1$, $Y_2$ and $Y_3$ each stands for an alkylene group or the radical of a cyclic organic ring system with 5 or 6 carbon atoms, and the sum of m, n, and t is 2 or 3, and $R_1$ denotes hydrogen or the radical of an amine of the formula $N(R_2)(R_3)$, wherein $R_2$ and $R_3$ stand for alkyl radicals with 1 to 4 carbon atoms, which method is characterized in that dihydracrylic acid amide of the general formula

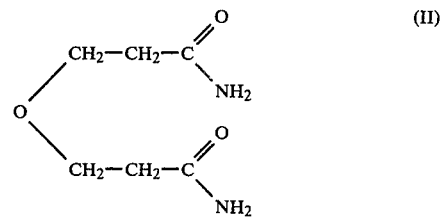

is transmitted with amines of the general formula

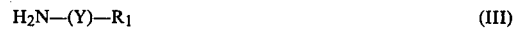

with elimination of ammonia and the resulting N-substituted β-carboxylic acid amides are converted into the desired N-substituted acrylamides at elevated temperatures by splitting out of water. The conversion of the N-substituted acrylamides with splitting out of water is preferably effected in the presence of a catalyst. The splitting out of water is preferably carried out at a temperature of 100° to 200° C. The second stage (splitting out of water) follows batch-wise at 70° to 200° C. or continuously at 250° to 450° C.

12 Claims, No Drawings

METHOD FOR MAKING N-SUBSTITUTED ACRYLAMIDES

The invention relates to a method for making N-substituted acrylamides. N-substituted alkyl-acrylamides have already been known for a long time. They can be obtained by reaction of acrylonitrile with 1-olefins (JACS 73, 1951, 4076), as well as by reaction of primary or secondary amines with an addition compound of maleic anhydride and triphenyl phosphine (Japanese Patent Publication No. 6920083). According to British Pat. No. 746,747, N-substituted acrylamides can be obtained by dehydrohalogenation of β-chloropropionic acid amides and, according to German DOS No. 2,344,070, by pyrolysis of β-methoxypropionic acid amides. They can further be obtained according to the Schotten-Baumann reaction by reaction of acrylic acid chloride with appropriate diamines (U.S. Pat. No. 2,951,907), by catalytic addition of functionalized amines to acetylenes under CO-atmosphere (U.S. Pat. No. 2,773,063), by reductive amination of diacetone acrylamide (J. Polym. Sci. 10 (1972) 595, as well as by pyrolysis of norbornene derivatives (German DOS No. 2,354,602). Finally, the compounds are also obtained according to the methods of German DOS No. 2,502,247, German DOS No. 2,656,682 and U.S. Pat. No. 3,878,247 by adding amines to acrylic or methacrylic esters with simultaneous aminolysis, N-substituted β-aminopropionic amides being obtained, which are pyrolytically split to the corresponding α,β-unsaturated N-substituted carboxylic acid amides.

All the known methods used expensive and/or highly toxic raw materials, require a large expenditure, and in most cases give only modest yields. It would, therefore be desirable to have a technically simple method, which gives the α, β-unsaturated N-substituted carboxylic acid amides in high yields.

This object is realized in accordance with the invention pursuant to which there is provided a method for making N-substituted acrylamides of the general formula

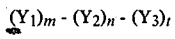

(I)

wherein
Y denotes a bivalent straight - or branched chain radical with 2 to 30, preferably 2 to 18, and particularly 2 to 6 carbon atoms, preferably a group of the formula $(Y_1)_m - (Y_2)_n - (Y_3)_t$,
$Y_1$, $Y_2$ and $Y_3$ each stands for an alkylene group or the radical of a cyclic organic ring system with 5 or 6 carbon atoms,
$m+n+t=2$ or 3, and
$R_1$ denotes hydrogen or the radical or an amine of the formula $N(R_2)$ $(R_3)$,
$R_2$ and $R_3$ stand for alkyl radicals with 1 to 4 carbon atoms,
which method is characterized in that dihydracrylic acid amide of the general formula

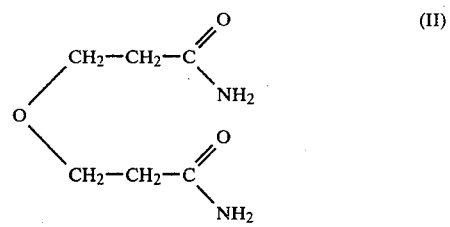

(II)

is transmitted with amines of the general formula $$H_2N - (Y) - R_1 \quad \text{(III)}$$

with elimination of ammonia and the resulting N-substituted dihydracrylic acid amides are converted into the desired N-substituted acrylamides at elevated temperatures by splitting out of water. The conversion of the N-substituted acrylamides with splitting out of water is preferably effected in the presence of a catalyst.

When Y stands for a group of the formula

then each of the radicals $Y_1$, $Y_2$ and $Y_3$ can denote a straight-chain or branched, possibly substituted alkylene group or the radical of a cyclic organic ring system with 5 or 6 carbon atoms, e.g. a cycloalkyl radical further optionally substituted by alkyl.

When Y is a branched-chain radical, it preferably is of the formula

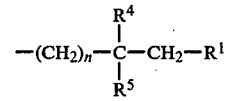

wherein
$R^4$ and $R^5$ are lower alkyl groups with 1 to 4 C atoms, preferably methyl groups,
n can be a number from 0 to 10, and
$R^1$ denotes an amino group $N(R^2)$ $(R^3)$.

When $R^1$ stands for the radical of an amine of the formula $N(R^2)$ $(R^3)$, then these radicals $R^2$ and $R^3$ which are identical or different can stand for straight - or branched-chain alkyl radicals, e.g. methyl, ethyl, propyl, isopropyl, n-butyl, etc.

Dihydracrylic acid amide represents the special case of a β-alkoxy-substituted propionic acid amide. By the catalytic ether splitting at elevated temperatures there results N-substituted acrylamide and alcohol, in this case, therefore N-substituted hydracrylic acid amide, which, under the particular reaction conditions, further gives N-substituted acrylamide and water. In contrast to alcohols, water is chemically inert in this reaction and does not tend to reverse the reaction, which must be prevented from splitting out alcohol by removing it by distillation from the mixture, the sump being thermally stressed for a prolonged period of time.

The dihydracrylic acid amide used as starting compound for the transamidation can readily be obtained from dihydracrylic acid nitrile (bis-(2-cyanoethyl)-ether) by catalyzed water addition (e.g. German DOS No. 2,065,667) or saponification with caustic soda/hydrogen peroxide (A. P. Teretjev, A. N. Kost and A. M. Berlin, J. Obsc. Chim. 26 (1956), 827,830). The compound precipitates from water in the form of crystals after evaporation. Dihydracrylic acid nitrile is available by addition of water to two molecules as well as by addition of hydracrylic acid nitrile (ethylene cyanhydrin, 3-hydroxypropionitrile) to one molecule of acrylonitrile under basic catalysis (O. Bayer Angew. Chem. 61 (1949), 229–241).

The transamidation can be effected at normal pressure with or without addition of catalysts. As catalysts, acids are particularly suited, acetic acid in amounts of about 0.5 to 1.0 mol % being particularly preferred.

The transamidation (first stage) is preferably effected in a temperature range of 100° to 200° C., and preferably 130° to 175° C.

Following the transamidation, water is pyrolytically split off from the resulting N,N'-disubstituted dihydracrylic acid amide, after which the resulting N-substituted acrylamide is isolated. The pyrolysis is preferably effected in the presence of acid or basic substances, either batch-wise or continuously. In case of a batch process, the pyrolysis takes place at 70° to 200° C., and preferably at 90° to 150° C. in the liquid phase. As acid catalysts, e.g. sulfuric acid, phosphoric acid or polyphosphoric acid can be used, and as basic catalysts, e.g. sodium or potassium hydroxide and/or carbonate or calcium and/or barium oxide can be used.

If a continuous process is employed, the pyrolysis is effected at 250° to 450° C. in the gaseous phase. The transamidated product is carefully evaporated, preferably under vacuum, e.g. by means of a thin film evaporator, and the vapors are passed through a reaction tube heated to 250° to 450° C. and filled with a solid dehydration catalyst, where the splitting into water and N-substituted acrylamide takes place. As catalyst in this manner of procedure, inorganic oxides with acid or basic character, such as aluminum oxide, silicon oxide or barium oxide, are used. The same may further be impregnated if need be. Dehydrated product and reaction water are then collected and condensed in fractions.

The products obtained by the process are usable for many purposes in industry. Examples thereof are given in German DOS No. 2,344,070. The products can, among other things, be polymerized and are suited as flocculation and retention agents in the form of their polymers and/or copolymers with other suitable comonomers, possibly after quaternization.

The invention will be explained more fully in the following examples:

EXAMPLE 1

N-(3-Dimethylaminopropyl) acrylamide 320.4 g (2.0 mols) dihydracrylic acid amide are heated with 429.2 g (4.2 mols) 3-dimethylaminopropylamine and 4 ml acetic acid for a period of 8 hours over a temperature span of 135° to 160° C. until ammonia generation is ended. 4.5 g orthophosphoric acid and 9.0 g polyphosphoric acid are added and 534 g liquid distilled at $bp_{10}=142°$ to 152° C. Upon re-distillation, after a fore-run of 36 gm water there are obtained 398 g (2.6 mols=64% of the theory) of product with $bp_{0.1}=102°$ to 104° C.

NMR (CDCl$_3$): δ=1.55 to 1.95 (m.2); 2.25 (s.6); 2.4 (t.2); 3.1 to 3.55 (m.2); 5.45 to 6.3 (m.3).

EXAMPLE 2

N-(N',N',2,2-Tetramethyl-3-aminopropyl)acrylamide 320.4 g (2.0 mols) dihydracrylic acid amide are heated with 546.8 g (4.2 mols) N,N,2,2-tetramethylpropanediamine-1,3 (dimethylaminoneopentylamine) and 4 ml acetic acid for 8 hours over a temperature span of 145° to 170° C. until ammonia generation is ended. 4.5 g orthophosphoric acid and 9.0 g polyphosphoric acid are added and the mass is distilled to give 557 g of liquid $bp_{10}=140°$ to 150° C. By re-distillation, after a fore-run of water, there are obtained 430 g (2.3 mols=58% of theory) of product $bp_{0.1}=94°$ to 98° C.

NMR (CDCl$_3$): δ=0.9 (s,6); 2.3 (m,8); 3.15 (d,2); 5.3 to 6.5 (m,3); 8.0 (m,1).

EXAMPLE 3

N-(3-Dimethylamino-propyl)acrylamide 320.4 g (2.0 mols) dihydracrylic acid amide are heated with 429.2 g (4.2 mols) 3-dimethylaminopropylamine and 4 ml acetic acid for 8 hours over a temperature span of 135° to 160° C. until ammonia generation is ended. Thereafter the volatile components are drawn off under high vacuum up to 100° C., whereby there are obtained 660 g of a yellow-brown oil which crystallizes at room temperature.

NMR (CDCl$_3$): δ1.45 to 2.0 (q,4); 2.1 to 2.6 (m,8); 2.25 (s,12); 3.1 to 3.6 (q,4); 3.7 (t,4); 7.2 (m,2).

600 g (2.0 mols) N,N'-disubstituted hydracrylamide are melted, successively evaporated in a thin film evaporator (temperature 300° C., vacuum 0.2 mbar) and the vapors passed through a reaction tube (100 cm length, 3 cm diameter) filled with aluminum oxide (spheres, 5–8 mm) and heated externally to 300° C. by a heating band. During the two hour process there are obtained 525 g (3.4 mols=84% of theory) N-(3-dimethylamino-propyl)acrylamide.

EXAMPLE 4

N-(N',N',2,2-Tetramethyl-3-aminopropyl)acrylamide 320.4 g (2.0 mols) dihydracrylic acid amide are heated with 546.8 g (4.2 mols) N,N,2,2-tetramethylpropanediamine-1,3 and 4 ml acetic acid for 8 hours over a temperature span of 145° to 120° C. until ammonia generation is ended. Thereafter the volatile components are drawn off up to 100°0 C. under high vacuum whereby 773 g of yellow-brown oil are obtained.

NMR (CDCl$_3$): δ=1.1 (s,12); 2.1 to 2.7 (m,8); 2.3 (s,12); 3.15 (d,4); 3.75 (t,4); 7.75 (m,2).

773 g (2.0 mols) N,N'-disubstituted dihydracrylamide are melted, successively evaporated in a thin film evaporator (temperature 300° C., vacuum 0.2 mbar) and the vapors passed through a reaction tube (100 cm length, 3 cm diameter) filled with aluminum oxide (spheres, 5–8 mm) and heated externally to 300° C. by a heating band. During the two hour process there are obtained 645 g (3.5 mols=88% of theory) N-(N'N'',2,2-tetramethyl-3-aminopropyl) acrylamide.

It will be appreciated that the instant specification and examples are set forth by way of illustration and not limitation, and that various modifications and changes may be made without departing from the spirit and scope of the present invention.

What is claimed is:

1. A process for the preparation of an N-substituted acrylamide of the formula

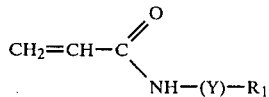

in which
- Y is a divalent alkylene radical with 2 to 30 carbon atoms;
- $R_1$ is hydrogen or a radical of the formula $-N(R_2)(R_3)$, and
- $R_2$ and $R_3$ each independently is alkyl of 1 to 4 carbon atoms, comprising transamidating dihydracrylic acid amide of the formula

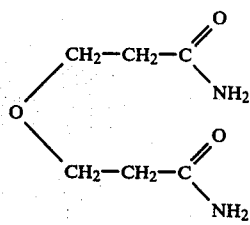

with an amine of the formula

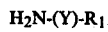

$H_2N-(Y)-R_1$ thereby simultaneously eliminating ammonia and forming the corresponding amide, and splitting out water from the corresponding amide at elevated temperature.

2. A process according to claim 1, in which
- Y is a divalent alkylene radical with 2 to 6 carbon atoms, and m, n and t are integers from 0 to 3 totaling 2 or 3.

3. A process according to claim 1 wherein the transamidation is effected at a temperature of about 100° to 200° C.

4. A process according to claim 1, wherein the transamidation is effected in the presence of a catalytic quantity of an acid.

5. A process according to claim 4, wherein the catalyst is acetic acid.

6. A process according to claim 1, wherein the splitting out of water is effected in the presence of acidic or basic substances.

7. A process according to claim 1, wherein the splitting out of water is effected batchwise at a temperature of about 70° to 200° C.

8. A process according to claim 1, wherein the splitting out of water is effected continuously at a temperature of about 250° to 450° C.

9. A process according to claim 8, wherein the water is split out of the transamidated product in vapor phase.

10. A process according to claim 9, wherein the transamidated product is evaporated and water is split out of the vapor over a solid catalyst.

11. A process according to claim 10, wherein the catalyst comprises at least one inorganic acidic or basic oxide selected from the group consisting of $Al_2O_4$, $SiO_2$ and $Ba_2O$.

12. A process according to claim 1 in which Y is a divalent alkylene radical with 2 to 18 carbon atoms.

* * * * *